United States Patent
Zou et al.

(10) Patent No.: US 10,655,158 B2
(45) Date of Patent: May 19, 2020

(54) BACTERIAL COUNTING METHOD

(71) Applicant: Jiangsu University, Zhenjiang, Jiangsu (CN)

(72) Inventors: Xiaobo Zou, Jiangsu (CN); Zhihua Li, Jiangsu (CN); Jiyong Shi, Jiangsu (CN); Xiaowei Huang, Jiangsu (CN); Xucheng Zhou, Jiangsu (CN); Xuetao Hu, Jiangsu (CN)

(73) Assignee: Jiangsu University, Zhenjiang, Jiangsu (CN)

( * ) Notice: Subject to any disclaimer, the term of this patent is extended or adjusted under 35 U.S.C. 154(b) by 106 days.

(21) Appl. No.: 15/572,555

(22) PCT Filed: Mar. 30, 2016

(86) PCT No.: PCT/CN2016/077794
§ 371 (c)(1),
(2) Date: Nov. 8, 2017

(87) PCT Pub. No.: WO2017/107333
PCT Pub. Date: Jun. 29, 2017

(65) Prior Publication Data
US 2018/0155755 A1 Jun. 7, 2018

(30) Foreign Application Priority Data
Dec. 21, 2015 (CN) .......................... 2015 1 0971248

(51) Int. Cl.
C12Q 1/06 (2006.01)
C12M 1/34 (2006.01)
G01N 15/06 (2006.01)
G01N 15/10 (2006.01)
G01N 15/00 (2006.01)

(52) U.S. Cl.
CPC ................ C12Q 1/06 (2013.01); C12M 1/34 (2013.01); G01N 15/0606 (2013.01); G01N 15/0656 (2013.01); G01N 15/1031 (2013.01); G01N 2015/0065 (2013.01); G01N 2015/1062 (2013.01)

(58) Field of Classification Search
CPC ....... C12Q 1/06; C12M 1/34; G01N 15/0656; G01N 15/0606; G01N 15/1031; G01N 2015/1062
See application file for complete search history.

(56) References Cited

U.S. PATENT DOCUMENTS

| 4,528,270 A | 7/1985 | Matsunaga |
| 2004/0175780 A1 | 9/2004 | Li et al. |
| 2007/0060815 A1* | 3/2007 | Martin ................ A61B 5/0408 600/372 |

FOREIGN PATENT DOCUMENTS

| CN | 101003830 A | | 7/2007 |
| CN | 101216449 A | * | 7/2008 |
| CN | 101216449 A | | 7/2008 |
| CN | 104198558 A | | 12/2014 |
| CN | 104407031 A | | 3/2015 |
| CN | 105067694 A | | 11/2015 |

OTHER PUBLICATIONS

Sivaprasad et al. Glassy Carbon Electrode Modified With Polyaniline Based Nanosensors for Electrochemical Determination of Aurone Flavonoid; International Journl of PharmaSciences and Research, vol. 6, No. 1, pp. 129- (Year: 2015).*
Zhihua et al. Bacteria Counting Method Based on Polyaniline/Bacteria Thin Film; Biosensors and Bioelectronics, vol. 81, pp. 75-79. (Year: 2016).*
International Search Report for PCT/CN2016/077794, dated Jul. 26, 2016.
Gao et al., "On bacteria biosensor based on E. coli modified carbon paste electrode by cyclic voltammetry," Journal of Shenyang Normal University (Natural Science Edition) 29(2):305-308 (2011).

* cited by examiner

Primary Examiner — Juliet C Switzer
Assistant Examiner — Paul C Martin
(74) Attorney, Agent, or Firm — Medler Ferro Woodhouse Mills PLLC

(57) ABSTRACT

Disclosed is a bacterial counting method, comprising the following steps, S1: preparing a polyaniline/bacterial composite film on the surface of a glassy carbon electrode by electric polymerization; S2: drawing the standard curve of the polyaniline/bacterial composite film modified electrode; and S3: determining the bacterial concentration of the bacteria solution sample to be tested according to the standard curve obtained in step S2. The method does not require the cultivation of the bacteria in the implementation process, such that same takes a short time and is easy to operate; the method uses aniline as the main reagent, and the consumption of the solution to be tested is small, such that the testing cost is low and the equipment is simple; the method has the advantages of a good repeatability and a wide detection linear range; and the method is an easy to operate, short time-consuming, and low cost bacterial counting method. The method is a bacterial counting method based on the polyaniline/bacterial composite film, and can achieve rapid and accurate detection of the bacterial thallus concentration.

5 Claims, 2 Drawing Sheets

(a)

(b)

(a)

(b)

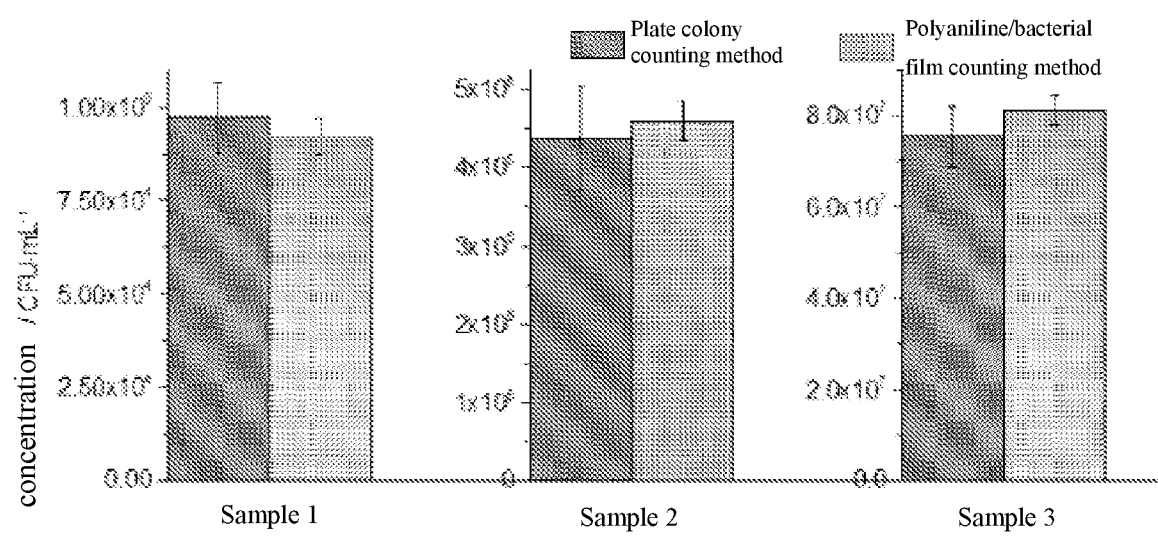
Fig. 4
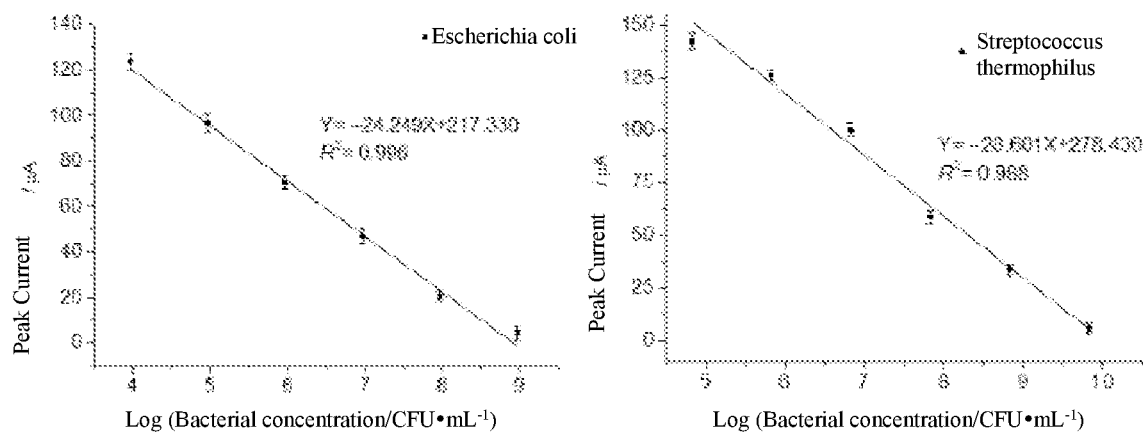
Fig. 5
Fig. 6

BACTERIAL COUNTING METHOD

FIELD OF THE INVENTION

The present invention belongs to the fields of material science and microbiology, and particularly relates to a bacteria counting method based on a polyaniline/bacterial composite film.

BACKGROUND OF THE INVENTION

It will be of great importance for the detection of the cell concentration of bacteria in the fields of microbial fermentation, environmental monitoring, foods quality inspection, etc. Currently, the common bacteria counting method is culture method, including a plate counting method and a MPN method.

The plate counting method is a national standard inspection method for detecting the total number of bacterial colonies (see reference: GB/T 4789.2-2010 Microbiological examination of food hygiene—Detection of aerobic bacterial count [S]), which is a standard method for judging the accuracy of other counting methods. The method is accurate in single colony counting in a dish, however, as the bacterial colonies in the culture dish are uniform in density, it will be subjective and inaccurate in the artificial observation and counting of adhesion colonies. As a whole, the method is complex in operation, long in time consumption, large in error and low in efficiency.

MPN is a diluent culture counting method. The method is suitable for detecting foods with a large number of competitive bacteria and raw materials thereof and untreated food containing a little amount of *Staphylococcus aureus*. The MPN method is a common indirect counting method. However, there is a certain limitation for such method.

Such culture methods have the defects of long time consumption, strict sterile operation, complex procedures, high labor and large influence by the culture condition.

In order to overcome the defects of the culture method, a plurality of counting methods are widely used. Among these methods, the fluorescence microscope counting method and the flow cytometry counting method are reliable and widely accepted. For the fluorescence microscope counting method, the fluorescence microscope use ultraviolet rays as a light source for irradiating detected objects to make them emit fluorescent light, and then, the shapes, positions and quantity of the objects are observed under the microscope. In the flow cytometry counting method, particles passing through the laser beam are counted via laser. When particles or cells pass through the laser beam, there will be refraction and reflection on light rays. The refraction signal and the reflection signal are recorded by a detector. A peak will be generated as soon as a cell passes through the laser beam, and finally, the number of peaks is recorded.

Although such two methods have the characteristics of quickness and accuracy, equipment is expensive and the cost of using and maintenance is high. Hence, it will have the important value to seek a bacteria counting method with simple and quick operation and low cost.

SUMMARY OF THE INVENTION

In order to solve the defects in the prior art, the present invention, provides a bacteria counting method with simple operation, short time consumption and low cost, which can realize the quick and accurate detection of the cell concentration of bacteria.

The technical solution of the present invention is: a bacteria counting method, comprising the following steps:

S1: preparing a polyaniline/bacterial composite film on the surface of a glassy carbon electrode via the electro-polymerization method;

S2: drawing a standard curve of a modified electrode of the polyaniline/bacterial composite film; and S3: measuring the bacterial concentration of a bacteria solution sample to be measured according to the standard curve obtained in the step S2.

In the above-mentioned solution, the step S1 specially comprises the following steps:

1) preparation of standard bacterial suspension:
    preparing bacterial culture solution, carrying out autoclaved sterilization, inoculating proper amount of strains for culturing, and centrifuging and washing bacteria solution obtained after culturing to obtain the standard bacterial suspension;

2) fixing of bacteria on the surface of the glassy carbon electrode:
    pretreating the glassy carbon electrode, measuring its cyclic voltammetry curve until the potential difference of the oxidation-reduction peak is reduced to be within 80 mV, drying the glassy carbon electrode, dripping the standard bacterial suspension to the surface of the glassy carbon electrode, drying, and fixing bacteria to the surface of the glassy carbon electrode; and 3) polymerization of phenylamine on the electrode surface:
    putting the glassy carbon electrode fixing with the bacteria into sulfuric acid solution containing phenylamine, scanning via cyclic voltammetry, and making phenylamine polymerize on the surface of the glassy carbon electrode to obtain the polyaniline/bacterial composite film.

In the above-mentioned solution, the sulfuric acid solution is 0.5M, phenylamine is 0.1M, scanning is carried out with 1 to 20 cycles at a scanning rate of 5 to 100 mV/s in the cyclic voltammetry, the lower limit of voltage is −0.6 to 0V, and the upper limit of voltage is 0.75 to 1.2 V.

Preferably, the scanning is carried out with 10 cycles, the scanning rate is 50 mV/s, and the scanning voltage ranges from −0.2 to 0.9 V.

In the above-mentioned solution, the step S2 specially comprises the following steps:

1) carrying out gradient dilution of the standard bacterial suspension obtained in the step S1 sequentially to acquire bacterial suspensions with different concentrations;

2) preparing the polyaniline/bacterial composite film on the surface of the glassy carbon electrode respectively by utilizing the obtained bacterial suspensions with different concentrations in accordance with the step S1, and rinsing with distilled water, measuring its cyclic voltammetry curve in 0.1 M of $H_2SO_4$ solution at a scanning rate of 50 mV/s and under scanning voltage ranging from −0.2 to 0.9 V; and 3) drawing a standard curve of the modified electrode of the polyaniline/bacterial composite film by taking the logarithm of bacterial concentration as horizontal coordinates and taking peak current corresponding to the peak of the cyclic voltammetry curve obtained in 2) as vertical coordinates.

In the above-mentioned solution, the step S3 specially comprises the following steps:

1) preparing the polyaniline/bacterial composite film on the surface of the glassy carbon electrode by utilizing the bacterial suspension to be measured in accordance with the step S1, and measuring its cyclic voltammetry curve in accordance with the step S2; and 2) determining the peak current of the cyclic voltammetry curve, and calculating bacterial concentration in accordance with the standard curve of the modified electrode of the polyaniline/bacterial composite film obtained in the step S2.

Compared with the prior art, the present invention has the following advantages:

1. The polyaniline/bacterial composite film is prepared on the surface of the glassy carbon electrode via the electropolymerization method. The bacteria fixed to the surface of the glassy carbon electrode can hinder the polymerization of the phenylamine on the electrode surface, so that the prepared polyaniline/bacterial composite film has different electrochemical properties, which can realize the quick and accurate detection of the cell concentration of bacteria.

2. In the implementation process of the present invention, it is not necessary for the bacteria to be counted after being cultured like the conventional plate counting method, hence, the method of the present invention is short in time consumption and easy to operate.

3. In the present invention, phenylamine is used as a main reagent, and the consumption of the solution to be measured is little, hence, the detection costs are low, and equipment is simple.

4. The method of the present invention has the advantages of good repeatability and wide linearity range of detection for the measurement of the cell concentration of the same bacteria.

BRIEF DESCRIPTION OF THE FIGURES

FIG. 4 is the detection result comparison diagram of the bacterial suspension samples of *Bacillus subtilis* with different concentrations, under the plate colony counting method and the polyaniline/bacterial film counting method of the present invention.

FIG. 5 is the standard curve graph of the cyclic voltammetry curve of the modified electrode of the polyaniline/*Escherichia coli* film at 0.2 V peak current.

FIG. 6 is the standard curve graph of the cyclic voltammetry curve of the modified electrode of the polyaniline/*Streptococcus thermophilus* film at 0.2 V peak current.

DETAILED DESCRIPTION OF THE INVENTION

Hereunder the present invention will be further detailed in the specific embodiments of *Bacillus subtilis*, *Escherichia coli* and *Streptococcus thermophilus* with reference to the accompanying drawings, however, the protecting scope of the present invention is not limited to the embodiments.

Example 1

Phenylamine, sulfuric acid, yeast extract and tryptone used in the present invention are purchased from Sinopharm Group Chemical Reagent Co., Ltd., and phenylamine is used after being distilled under reduced pressure. In electrochemical measurement, the CHI660D electrochemical workstation is adopted (Shanghai Chenhua Instrument Co., Ltd.). In the present example, it will make description by taking *Bacillus subtilis* as an example, and strains are purchased from China Center of Industrial Culture Collection.

Figure 1:
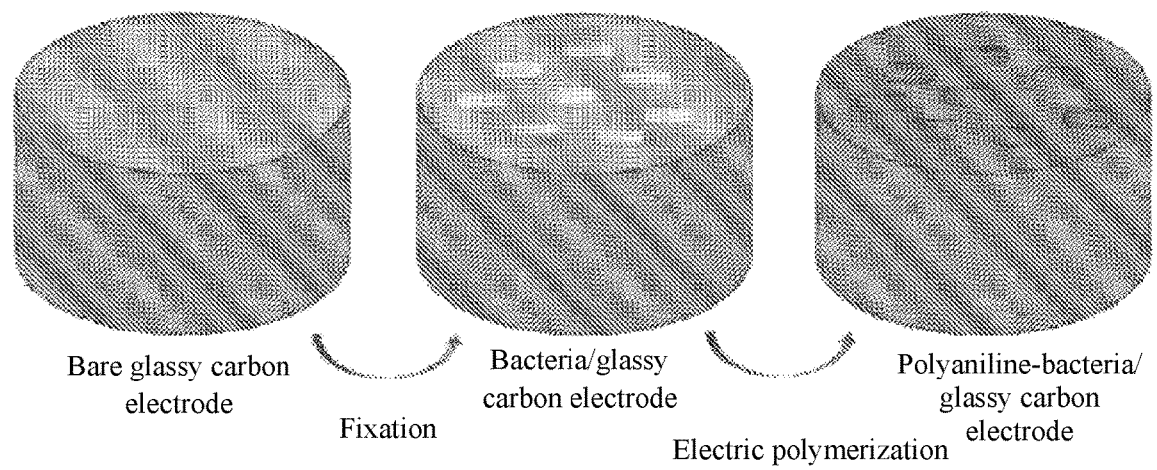
FIG. 1 is the schematic diagram of the integral preparation process of the polyaniline/bacterial composite film.
Figure 2:
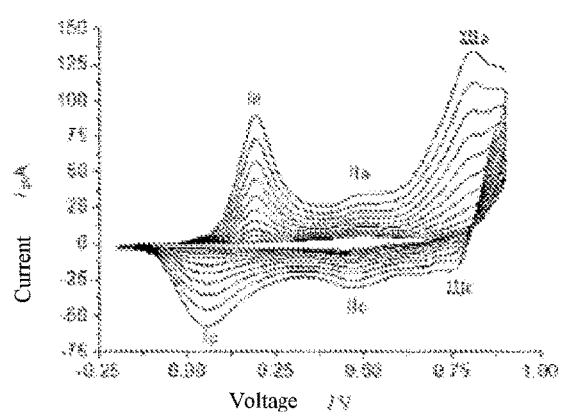
FIG. 2(a) is the change diagram of the cyclic voltammetry curve of the electrode in the process of preparing the polyaniline-bacterial composite film via the cyclic voltammetry.
FIG. 2(b) is the morphology comparison diagram of the prepared polyaniline/bacterial composite film and the pure polyaniline film.
Figure 2:
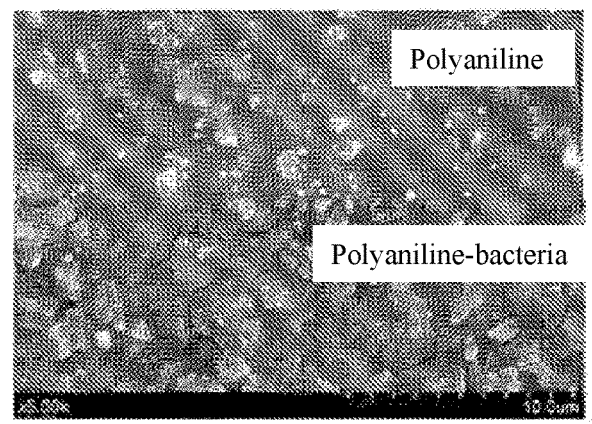

The bacteria counting method comprises the following steps:

S1. Preparing a polyaniline/bacterial composite film on the surface of a glassy carbon electrode via the electropolymerization method;

FIG. 1 shows the integral preparation process of the polyaniline/bacterial composite film, including the following steps:

(1) preparation of standard bacterial suspension:
taking 5 g of yeast extract, 10 g of tryptone and 10 g of sodium chloride, adding water to prepare 1 L of culture solution, regulating pH to 7.0 by using NaOH, carrying out autoclaved sterilization at temperature of 121° C. for 20 min, inoculating proper amount of *Bacillus subtilis* strains, and culturing in a constant temperature incubator at temperature of 37° C. for 20 h; centrifuging the obtained bacteria solution under 3500 g of centrifugal force at temperature of 4° C. for 10 min and then washing for 3 times to obtain standard *Bacillus subtilis* suspension, and measuring its cell concentration via the plate colony counting method, which is 5.33×10$^8$ CFU·mL$^{-1}$;

(2) fixing of bacteria on the surface of the glassy carbon electrode:
polishing the glassy carbon electrode sequentially by using abrasive paper for metallograph, 0.3 μm and 0.05 μm of Al2O3 powder, carrying out ultrasonic washing respectively by using ethanol and water, measuring the cyclic voltammetry (CV) curve of the glassy carbon electrode in 1 mM of $K_3[Fe(CN)_6]$ solution until the potential difference of the oxidation-reduction peak is reduced to be within 80 mV, and drying to ensure the consistent initial state of the electrode; dripping 10 μL of standard *Bacillus subtilis* suspension to the surface of the glassy carbon electrode, and drying in a drying oven at temperature of 50° C. for 15 min to fix bacteria to the surface of the glassy carbon electrode, and obtaining the bacteria/glassy carbon electrode; and (3) polymerization of phenylamine on the electrode:
putting the glassy carbon electrode fixing with bacteria into sulfuric acid solution (0.5M) containing 0.1 M of phenylamine, and scanning by taking the platinum filament electrode as the counter electrode and taking the silver/silver chloride electrode as the reference electrode via the cyclic voltammetry. In order to acquire higher detection sensitivity, preferably, the number of scanning cycles is 10, the scanning rate is 50 mV/s, the lower limit of voltage is −0.2 V, the upper limit of voltage is 0.9 V, and the polyaniline/*Bacillus subtilis* composite film is obtained. FIG. 2(a) is the change of the cyclic voltammetry curve of the electrode in the process of preparing the polyaniline/bacterial composite film via the cyclic voltammetry, in which there are 3 pairs of typical oxidation-reduction peaks: I a/I c, IIa/IIc, and IIIa/IIIc, indicating the successful polymerization of phenylamine on the electrode surface. In addition, the scanning current is gradually increased with the increase of the scanning cycles, which manifests the self-catalysis effect of polyaniline during the polymerization of polyaniline. FIG. 2(b) is the morphology comparison of the polyaniline/*Bacillus subtilis* composite film prepared at bacterial concentration of 5.33×105 CFU·mL−1 and the pure polyaniline film, two films are apparently different in morphology, indicating the fixing of stains possesses a large impact on the deposition of polyaniline on the electrode surface, which shows different electrochemical properties, and thereby providing basis for the quantitative determination of cell concentration.

S2. Drawing a standard curve of a modified electrode of the polyaniline/bacterial composite film:

Diluting the standard bacterial suspension with the concentration of 5.33×108 CFU·mL−1 obtained in the step S1 to be 1.066×108 CFU·mL−1, 5.33×107 CFU·mL−1, 5.33×106 CFU·mL−1, 1.066×106 CFU·mL−1, 5.33×105 CFU·mL−1 and 5.33×104 CFU·mL−1 sequentially, preparing the polyaniline/*Bacillus subtilis* composite film on the surface of the glassy carbon electrode by utilizing the obtained bacterial suspensions with different concentrations in accordance with the step S1, rinsing by using distilled water, and measuring its cyclic voltammetry curve in 0.1M of H2 SO4 solution. The scanning voltage ranges from −0.2 to 0.9 V, and scanning rate is 50 mV/s.

Figure 3:
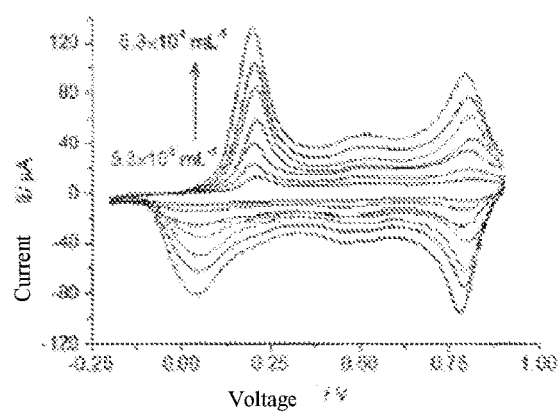
FIG. 3(a) is the cyclic voltammetry curve graph of the modified glassy carbon electrode of the polyaniline/bacterial composite film in 0.1M of $H_2SO_4$ solution prepared by using the bacterial suspension of *Bacillus subtilis* with different concentrations.
FIG. 3(b) is the standard curve graph of the cyclic voltammetry curve of the modified electrode of the polyaniline/*Bacillus subtilis* film at 0.2 V peak current.
Figure 3:
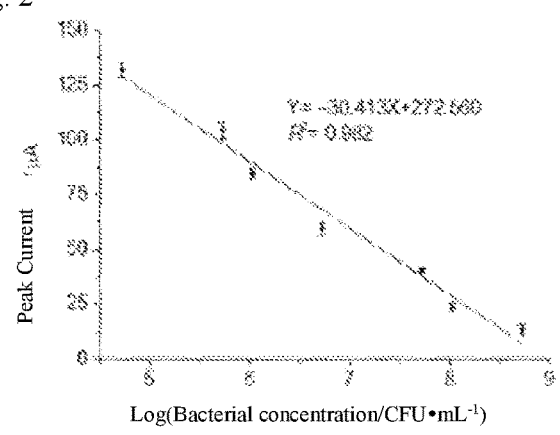

Drawing a standard curve of the modified electrode of the polyaniline/*Bacillus subtilis* composite film by taking the logarithm of bacteria concentration as horizontal coordinates X and taking peak current of the cyclic voltammetry curve at 0.2V as vertical coordinates Y. FIG. 3(a) is the cyclic voltammetry curve corresponding to the bacterial suspensions with different concentrations, and FIG. 3(b) is its peak current standard curve. As can be seen from FIG. 3, there is good linear relation between the peak current of the electrode at 0.2V and the logarithm of bacteria concentration: Y=−30.413X+272.560, and $R^2$=0.982.

S3. Measuring the bacterial concentration of a bacteria solution sample to be measured:

Preparing the polyaniline/*Bacillus subtilis* composite film by utilizing the bacterial suspension in accordance with the step S1, measuring the cyclic voltammetry curve of the film in 0.1 M of $H_2SO_4$ solution in accordance with the step S2, and calculating its cell concentration via the standard curve of the modified electrode of the polyaniline/*Bacillus subtilis* composite film obtained in the step S2 in accordance with the peak current of it at 0.2V. Table 1 and FIG. 4 are the measuring result comparison of the polyaniline/bacterial composite film counting method and the plate colony counting method. The result indicates that the mean value of the bacterial suspension concentration measured in the method of the present invention for 5 times is basically consistent with the measuring result of the plate colony counting method, but the relative standard deviation of the method is obviously inferior to that of the plate colony counting method, indicating that it has the higher stability. The polyaniline/bacterial composite film counting method is superior to the conventional plate colony counting method in the counting result.

TABLE 1

Result comparison of the *Bacillus subtilis* sample measured based on the polyaniline/bacterial composite film counting method and the plate colony counting method

| | Plate colony counting method | | Polyaniline/bacterial composite film counting method | |
|---|---|---|---|---|
| Number | Mean value (CFU · mL$^{-1}$) | Relative standard deviation | Mean value (CFU · mL$^{-1}$) | Relative standard deviation |
| Sample 1 | 9.72 × 10$^4$ | 9.57% | 9.21 × 10$^4$ | 5.21% |
| Sample 2 | 4.37 × 10$^5$ | 15.29% | 4.59 × 10$^5$ | 5.49% |
| Sample 3 | 7.54 × 10$^7$ | 8.73% | 8.11 × 10$^7$ | 3.87% |

Example 2

The method used for this example is the same as that of example 1, but the difference is that in this example, it will make description by taking *Escherichia coli* as an example, and strains are purchased from China Center of Industrial Culture Collection.

The standard *Escherichia coli* suspension with cell concentration of 9.26×108 CFU·mL$^{-1}$ is obtained in the same method as the step S1 in the example 1, and then is sequentially diluted to be 9.26×107 CFU·mL$^{-1}$, 9.26×106 CFU·mL$^{-1}$, 9.26×105 CFU·mL$^{-1}$, 9.26×104 CFU·mL$^{-1}$ and 9.26×103 CFU·mL$^{-1}$.

Drawing a standard curve of the modified electrode of the polyaniline/*Escherichia coli* composite film by taking the logarithm of *Escherichia coli* concentration as horizontal coordinates X and taking peak current of the cyclic voltammetry curve at 0.2V as vertical coordinates Y in accordance with the step S2 in example 1. As can be seen in FIG. 5, there is good linear relation between the peak current of the electrode at 0.2 V and the logarithm of *Escherichia coli* concentration: Y=−24.249 X+217.33, and $R^2$=0.996.

Measuring the sample of the *Escherichia coli* bacteria solution to be measured in accordance with step S3 in example 1. Table 2 is the result comparison of the *Escherichia coli* sample measured based on the polyaniline/bacterial composite film counting method and the plate colony counting method. The result indicates that the mean value of the bacterial suspension concentration measured in the method of the present invention for 5 times is basically consistent with the measuring result of the plate colony counting method, but the relative standard deviation of the method is obviously inferior to that of the plate colony counting method, indicating that it has the higher stability. The polyaniline/bacterial composite film counting method is also applied to the *Escherichia coli* sample.

TABLE 2

Result comparison of the *Escherichia coli* sample measured based on the polyaniline/bacterial composite film counting method and the plate colony counting method

| | | Items | | | |
|---|---|---|---|---|---|
| | | Plate colony counting method | | Polyaniline/bacterial composite film counting method | |
| | Number | Mean value (CFU · mL$^{-1}$) | Relative standard deviation | Mean value (CFU · mL$^{-1}$) | Relative standard deviation |
| *Escherichia coli* | Sample 1 | $8.12 \times 10^4$ | 8.66% | $8.72 \times 10^4$ | 4.31% |
| | Sample 2 | $5.23 \times 10^6$ | 15.29% | $4.97 \times 10^6$ | 5.19% |

Example 3

The method used for this example is the same as that of example 1 and example 2, but the difference is that in this example, it will make description by taking *Streptococcus thermophilus* as an example, and strains are purchased from China Center of Industrial Culture Collection.

Weighing 52.4 g of MRS bouillon culture-medium (purchased from Qingdao Haibo Biotechnology Co., Ltd.), heating to dissolve in 1 L of distilled water, carrying out autoclaved sterilization at temperature of 118° C. for 15 min, cooling, inoculating proper amount of *Streptococcus thermophilus* strains, and culturing in the constant-temperature incubator at temperature of 37° C. for 20 h. Centrifuging the obtained bacteria solution at temperature of 4° C. under 3500 g of centrifugal force for 10 min, and then washing for 3 times, obtaining the standard *Streptococcus thermophilus* suspension, measuring its cell concentration via the plate colony counting method, which is $6.72 \times 10^9$ CFU·mL$^{-1}$. Sequentially diluting the standard suspension to be $6.72 \times 10^8$ CFU·mL$^{-1}$, $6.72 \times 10^7$ CFU·mL$^{-1}$, $6.72 \times 10^6$ CFU·mL$^{-1}$, $6.72 \times 10^5$ CFU·mL$^{-1}$ and $6.72 \times 10^4$ CFU·mL$^{-1}$. Drawing a standard curve of the modified electrode of the polyaniline/*Streptococcus thermophilus* composite film by taking the logarithm of bacterial concentration as horizontal coordinates X and taking peak current of the cyclic voltammetry curve at 0.2V as vertical coordinates Y in accordance with the step S2 in the example 1. As can be seen from FIG. 6, there is good linear relation between the peak current of the electrode at 0.2V and the logarithm of bacterial concentration: $Y=-28.601 X+278.430$, and $R^2=0.988$.

Measuring the sample of the *Streptococcus thermophilus* bacteria solution to be measured in accordance with step S3 in example 1. Table 3 is the result comparison of the *Streptococcus thermophilus* sample measured based on the polyaniline/bacterial composite film counting method and the plate colony counting method. The result indicates that the mean value of the bacterial suspension concentration measured in the method of the present invention for 5 times is basically consistent with the measuring result of the plate colony counting method, but the relative standard deviation of the method is obviously inferior to that of the plate colony counting method, indicating that it has the higher stability. The polyaniline/bacterial composite film counting method is also applied to the *Streptococcus thermophilus* sample.

TABLE 3

Result comparison of the *Streptococcus thermophilus* sample measured based on the polyaniline/bacterial composite film counting method and the plate colony counting method

| | | Items | | | |
|---|---|---|---|---|---|
| | | Plate colony counting method | | Polyaniline/bacterial composite film counting method | |
| | Number | Mean value (CFU · mL$^{-1}$) | Relative standard deviation | Mean value (CFU · mL$^{-1}$) | Relative standard deviation |
| *Streptococcus thermophilus* | Sample 1 | $3.22 \times 10^8$ | 10.54% | $3.61 \times 10^8$ | 4.81% |
| | Sample 2 | $2.89 \times 10^5$ | 11.76% | $3.13 \times 10^5$ | 5.24% |

The above mentioned examples are the preferable embodiments of the present invention; however, the present invention is not limited to the above-mentioned embodiments. The person skilled in the art could make apparent improvement, replacement or change under the condition of not deviating from the essential content of the present invention, which belongs to the protection scope of the present invention.

The invention claimed is:

1. A bacteria counting method, comprising the following steps:
    (a) preparing a polyaniline/bacterial composite film on a surface of a glassy carbon electrode via an electropolymerization method, comprising:
        1) preparing a standard bacterial suspension, comprising:
            preparing a bacterial culture solution; carrying out autoclaved sterilization of the bacterial culture solution; inoculating a proper amount of strains for culturing; and centrifuging and washing the bacteria solution obtained after culturing to obtain the standard bacterial suspension;

2) fixing of bacteria on the surface of the glassy carbon electrode, comprising:

pretreating the glassy carbon electrode and measuring a cyclic voltammetry curve of the glassy carbon electrode, until a potential difference of the oxidation-reduction peak is reduced to be within 80 mV; drying the glassy carbon electrode; dripping the standard bacterial suspension to the surface of the glassy carbon electrode; and drying, thereby fixing bacteria to the surface of the glassy carbon electrode; and 3) polymerization of phenylamine on the electrode surface, comprising:

putting the glassy carbon electrode fixed with the bacteria into a sulfuric acid solution containing phenylamine; scanning via cyclic voltammetry; and making phenylamine polymerize on the surface of the glassy carbon electrode to obtain the polyaniline/bacterial composite film;

(b) drawing a standard curve of a modified electrode of the polyaniline/bacterial composite film, comprising:

1) carrying out gradient dilution of the standard bacterial suspension obtained in step (a) sequentially to acquire bacterial suspensions with different concentrations;

2) preparing a polyaniline/bacterial composite film on the surface of the glassy carbon electrode for each concentration of the bacterial suspensions with different concentrations according to step (a) and measuring a cyclic voltammetry curve for each concentration of bacterial suspension; and 3) drawing a standard curve of the modified electrode of the polyaniline/bacterial composite film by taking the logarithm of bacterial concentration as horizontal coordinates and taking peak current corresponding to the peak of the cyclic voltammetry curve obtained in step (b)(2) as vertical coordinates; and (c) measuring a bacterial concentration of a bacteria solution sample according to the standard curve obtained in the step (b).

2. The bacteria counting method according to claim 1, wherein the sulfuric acid solution is 0.5M; phenylamine is 0.1M; scanning is carried out with 1 to 20 cycles at a scanning rate of 5 to 100 mV/s in the cyclic voltammetry; a lower limit of scanning voltage is −0.6V to 0V; and an upper limit of scanning voltage is 0.75V to 1.2V.

3. The bacteria counting method according to claim 2, wherein scanning is carried out with 10 cycles; the scanning rate is 50 mV/s; and the scanning voltage ranges from −0.2V to 0.9V.

4. The bacteria counting method according to claim 1, wherein step (b)(2) comprises:

preparing the polyaniline/bacterial composite film on the surface of the glassy carbon electrode for each concentration of the bacterial suspensions with different concentrations according to step (a); rinsing the polyaniline/bacterial composite film with distilled water; and measuring the cyclic voltammetry curve for each concentration of bacterial suspension in 0.1 M of $H_2SO_4$ solution at scanning rate of 50 mV/s and under scanning voltage ranging from −0.2 to 0.9V.

5. The bacteria counting method according to claim 1, wherein step (c) comprises:

1) preparing a further polyaniline/bacterial composite film on the surface of the glassy carbon electrode by utilizing the bacterial solution sample to be measured in accordance with step (a); and measuring a cyclic voltammetry curve of the bacterial solution sample to be measured; and 2) determining peak current of the cyclic voltammetry curve of the bacterial solution sample to be measured, and calculating bacterial concentration in accordance with the standard curve of the modified electrode of the polyaniline/bacterial composite film obtained in the step (b).

* * * * *